United States Patent [19]

Singh

[11] Patent Number: 4,584,376

[45] Date of Patent: Apr. 22, 1986

[54] 1-HETEROCYCLICTHIO-1-CYCLO-PROPANECARBONITRILES AS CROP PROTECTANTS

[75] Inventor: Rajendra K. Singh, Maryland Heights, Mo.

[73] Assignee: Monsanto Company, St. Louis, Mo.

[21] Appl. No.: 440,771

[22] Filed: Nov. 10, 1982

[51] Int. Cl.[4] .................. C07D 249/12; C07D 277/36; C07D 233/30; C07D 239/38

[52] U.S. Cl. ........................................ 544/316; 71/90; 71/92; 544/239; 544/408; 548/189; 548/213; 548/255; 548/263; 548/337; 548/375

[58] Field of Search ............... 548/189, 213, 255, 263, 548/337, 375; 544/239, 408, 316

[56] References Cited

U.S. PATENT DOCUMENTS

| | | |
|---|---|---|
| 3,954,729 | 5/1976 | Sato et al. .................... 260/239 B |
| 4,071,423 | 1/1978 | Pitt .................................. 204/158 R |
| 4,120,690 | 10/1978 | Cahoy .................................. 71/90 |
| 4,238,614 | 12/1980 | Henrick ............................. 546/301 |
| 4,251,527 | 2/1981 | Gullo et al. ....................... 424/249 |
| 4,252,819 | 2/1981 | Hirata et al. ..................... 424/285 |
| 4,449,998 | 5/1984 | Lavanish ............................. 71/92 |
| 4,451,281 | 5/1984 | Elbe .................................... 71/92 |
| 4,451,282 | 5/1984 | Knops ................................. 71/92 |
| 4,452,625 | 6/1984 | Lorsson .............................. 71/76 |
| 4,452,626 | 6/1984 | Pilgrom .............................. 71/92 |
| 4,452,628 | 6/1984 | Adams ................................ 71/93 |

*Primary Examiner*—Robert Gerstl
*Attorney, Agent, or Firm*—J. Timothy Keane; Paul D. Matukaitis

[57] ABSTRACT

Certain 1-heterocyclicthio-1-cyclopropanecarbonitriles have been found to reduce herbicidal injury of certain food crops due to the application thereto of herbicides that kill or control weeds that impede the yield of crops.

5 Claims, No Drawings

1-HETEROCYCLICTHIO-1-CYCLOPROPANECARBONITRILES AS CROP PROTECTANTS

This invention relates to novel and useful 1-heterocyclicthio-1-cyclopropanecarbonitriles. The invention also relates to such cyclopropanecarbonitriles compositions and methods for reducing injury to crop plants by herbicides, which comprise treating the crop plant locus or seed of the crop plant with an effective safening amount of the carbonitrile, as will be described more fully below. Seeds coated with such carbonitriles are also within the scope of the present invention.

BACKGROUND OF THE INVENTION

Herbicides are very useful for controlling certain weeds and unwanted grasses in the presence of growing crops. However, many of the herbicides injure certain crop plants by slowing growth and development at application rates necessary to stunt or kill the weeds and grasses. Accordingly, many herbicides cannot be used for controlling weeds in the presence of certain crops. Obviously, a safening agent, (also referred to as herbicide antidote or seed protectant) consisting of a composition that can be used to treat the seed of the crop plant, the plant crop locus or the crop plant itself, resulting in a reduction of injury due to appplication of the herbicide but without an unacceptable corresponding reduction of herbicidal action on the weeds or grasses, would be quite beneficial. A new class of safening agents for doing that is provided by the present invention.

DESCRIPTION OF THE INVENTION

In accordance with the novel aspects of the present invention, injury to crop plants, such as sorghum, wheat and rice due to application thereto of herbicides, especially acetanilide herbicides such as 2-chloro-2',6'-diethyl-N-(methoxymethyl)acetanilide (whose common is alachlor); and 2-chloro-2',6'-diethyl-N-(butoxymethyl)acetanilide (whose common name is butachlor), may be reduced without a corresponding reduction in injury to the weeds by application to the crop plant locus or the seed of the crop plant prior to planting of an effective amount of a safening agent having the structural formula

where Het represents a 5-membered or 6-membered heterocyclic group. The N-containing heterocyclic group includes the following radicals

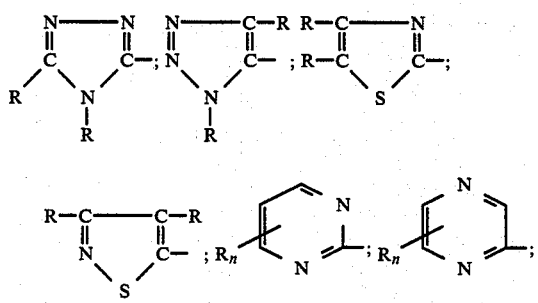

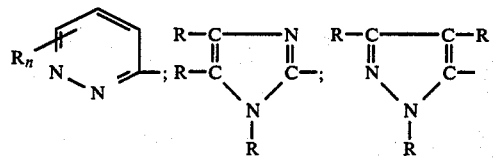

where R is hydrogen, $C_1$–$C_5$ alkyl, $C_1$–$C_5$ alkoxy, $C_1$–$C_5$ haloalkyl, halogen, $C_1$–$C_5$ haloalkoxy, amino, phenyl, benzyl and phenyl substituted with up to three groups individually selected from the class consisting of $C_1$–$C_5$ alkyl, $C_1$–$C_5$ alkoxy, $C_1$–$C_5$ haloalkyl, nitro and halogen and n is 0-3.

The term "$C_1$–$C_5$ alkyl" is intended to mean straight and branched alkyl radicals having 1 to 5 carbon atoms including, for example, methyl, ethyl, n-propyl, isopropyl, n-butyl, sec-butyl, tert-butyl, n-pentyl, isopentyl, etc. The term "$C_1$–$C_5$ alkoxy" is intended to mean straight or branched chain alkoxy radicals including, for example, methoxy, ethoxy, n-propoxy, isopropoxy, n-butoxy, sec-butoxy, tert-butoxy, n-pentoxy, isopentoxy, etc. The term "haloalkyl" is intended to mean alkyl moieties having 1–5 carbon atoms wherein at least one hydrogen atom has been replaced by a halogen including, for example, chloromethyl, iodobutyl, dichloroethyl, dibromopropyl, trichloromethyl, trifluoromethyl, etc. The term "halogen" as used herein includes chloro, bromo, fluoro and iodo. The term $C_1$–$C_5$ haloalkoxy is intended to mean straight or branched chain alkoxy radical having 1–3 halogen substituents including for example, fluoromethoxy, chloroethoxy, fluoroethoxy, fluoropropoxy, chlorobutoxy and the like. Illustrative of the substituted phenyl groups are monosubstituted phenyl wherein the substituent is in the ortho, meta or para position, for example, methylphenyl, butylphenyl, methoxyphenyl, butoxyphenyl, fluorophenyl, chlorophenyl, bromophenyl, iodophenyl, trifluoromethylphenyl, nitrophenyl and the like and the di- and tri-substituted phenyls wherein the substituents are the same or different and are located in the 2, 3, 4, 5 or 6 positions of the phenyl ring, for example, dichlorophenyl, difluorophenyl, methylchlorophenyl, butoxyfluorophenyl, methylbutylphenyl, methoxybutoxyphenyl, dimethoxyphenyl, methylnitrophenyl, trimenthylphenyl, tributoxyphenyl and the like.

The amount of the safening agent employed in the methods and compositions of the invention will vary depending upon the particular herbicide with which the agent is employed, the rate of application of the herbicide, the particular food crop seed to be protected, and the manner of application and use of the safening agent. In each instance the amount of agent employed is a safening effective amount, i.e., the amount which reduces or protects against crop injury that otherwise would result from the application of the herbicide. Furthermore, the amount of safening agent employed will be less than an amount that will substantially injure the crop seed.

The safening agent can be applied to the crop plant seed locus in a mixture with the selected herbicide. For example, where the crop seed is first planted, a suitable mixture of safening agent and herbicide wheter in a homogenous liquid, emulsion, suspension or solid form can be topically applied to the surface of or incorporated in the soil in which the seeds have been planted. The herbicide will reduce or eliminate the presence of undersirable weed and grass plants. Where the herbicide would by itself injure the crop seeds, the presence of the safening agent will reduce or eliminate the injury to the crop otherwise ensuing from the application of herbicide. It will be appreciated that it is not essential that the application of herbicide and the safening agent to the plant locus be made using the selected herbicide and safening agent in the form of a mixture or composition. The herbicide and the safening agent may be applied to the plant locus in a sequential manner. For example, the safening agent may be applied to the plant locus and thereafter the herbicide is applied. The reverse order of the application of the safening agent and herbicide is also within the purview of the present invention. In such case the herbicide is first applied to the plant locus and thereafter the safening agent is applied.

Furthermore, the application of the safening agent can be made directly on the seed before planting. In this practice, a quantity of crop seeds is first coated with the safening agent. The coated seeds are thereafter planted. Then, the herbicide is topically applied to soil in which the precoated seeds have been planted.

By application to the "plant locus" is meant application to the plant growing medium, such as soil, as well as the seeds, emerging seedlings, roots, stems, leaves, or other plant parts.

The amount of herbicide employed is well within the skill of the art and is disclosed in various patents.

The novel heterocyclic compounds can be prepared by reacting a heterocylic thioacetonitrile with 1,2-dihaloethane, preferably with 1,2-dibromoethane in the presence of a base catalyst as shown, for example, in the equation setforth at the top of Table 1. The selected thioacetonitrile and dihaloethane may be reacted directly together without the use a solvent or may be reacted in an inert solvent at a temperature of from about 0° C. to about 150° C., preferably from about 20° C. to about 80° C., and at a pressure from about 1 to 10 atmospheres, preferably from about 1 to 2 atmospheres. Normally, the reaction is conducted at atmospheric pressure, although the pressure can be lower or higher than atmopsheric if needed to control the reaction or maintain the reactants and products in the desired phrase. Useful inert solvents include aliphatic and aromatic hydrocarbons, such as methylene chloride, etc. The reaction is carried out in the presence of a quaternary ammonium catalyst, such as tetraethyl ammonium chloride, triethylbenzyl ammonium chloride and the like in an amount of from about 0.1 to 1.0% by weight, based on the weight of the reactants. The molar ratio of acetonitrile to dihaloethane can vary from about 1:1.15 to about 1:3. An excess amount of dihaloethane is preferred to insure complete reaction of the acetonitrile.

Reaction times can vary from a few minutes to several days. Usually reaction times of 1–24 hours are sufficient.

The following examples are presented for illustrative purposes only and are not intended as a restriction on the scope of the invention. All parts are by weight unless otherwise indicated. It should be noted that the 1-heterocyclicthio-1-cyclopropanecarbonitriles of the present invention can be prepared according to the general procedure described in Example 1. In Table 1, data of various and several compounds, all of which were prepared by such procedure, have been setforth.

EXAMPLE 1

The 1-heterocyclicthio-1-cyclopropanecarbonitriles are prepared by the cyclopropanation of α-heterocyclicthioacetonitriles.

To prepare the α-heterocyclicthioacetonitrile a heterocyclic thiol was reacted with a haloacetonitrile in a known manner. The heterocyclicthioacetonitrile used in the preparation of the carbonitrile compounds identified in Table 1 were prepared as follows. The selected mercaptoheterocyclic (0.1 mole) was dissolved in tetrahydrofuran (100 ml) and triethylamine (0.125 mole) was slowly added to the mixture. Then, chloroacetonitrile (0.11 mole) was added to the mixture. The resulting reaction mixture was stirred overnight. The mixture was then diluted with 100 ml of diethyl ether with the result that triethylammonium hydrochloride precipitated which was removed by filtration with the precipitate being washed with additional ether. The combined filtrate was concentrated by evaporating the ether. The produced α-heterothioacetonitrile was purified by a distillation procedure in the case of a normally liquid product or by crystallization from 95% ethanol in the case of a normally solid product.

In preparing the compounds of Table 1, a mixture of the appropriately selected α-heterothioacetonitrile (0.1 mole), 1,2-dibromoethane (0.3 mole) and triethylbenzyl ammonium chloride (TEBA) (1.0 gm), as catalyst, was stirred. To the stirred mixture 50 ml of 50% sodium hydroxide solution was added. In cases where the reaction mixture became viscous, the mixture was diluted with 50 ml of methylene chloride. Waterbath cooling was applied in the case where the reaction temperature exceeded 50° C. Stirring was continued 2–4 hours. The reaction mixture was diluted with 100 ml of water and extracted with 100 ml of methylene chloride (4X). The resulting organic layer containing the carbonitrile was washed with water, brine, and dried over magnesium sulfate. The solvent was removed by evaporation. The nitrile product was crystallized or chromatographed to purify the product as appropriate.

TABLE 1

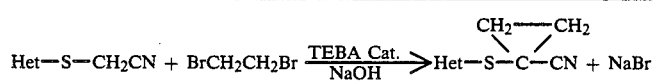

| Compound No. | Het | % Yield | 1. MP or 2. BP °C. | % C Calc'd | % C Found | % H Calc'd | % H Found | % N Calc'd | % N Found | % S Calc'd | % S Found |
| --- | --- | --- | --- | --- | --- | --- | --- | --- | --- | --- | --- |
| 1 | 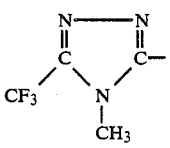 | 27 | 90–92(1) | 38.7 | 38.8 | 2.8 | 2.9 | 22.6 | 22.6 | 12.9 | 13.0 |

TABLE 1-continued $$\text{Het}-S-CH_2CN + BrCH_2CH_2Br \xrightarrow[\text{NaOH}]{\text{TEBA Cat.}} \text{Het}-S-\underset{\underset{CH_2-CH_2}{\diagup}}{C}-CN + NaBr$$

| Compound No. | Het | % Yield | 1. MP or 2. BP °C. | % C Calc'd | % C Found | % H Calc'd | % H Found | % N Calc'd | % N Found | % S Calc'd | % S Found |
|---|---|---|---|---|---|---|---|---|---|---|---|
| 2 | Phenyl-thiazolyl | 69 | 63–65(1) | 60.4 | 61.1 | 3.9 | 3.8 | 10.8 | 10.1 | | |
| 3 | 4-methyl-pyrimidinyl | 25 | 77–78(1) | 56.5 | 56.3 | 4.7 | 4.8 | 22.0 | 21.9 | | |
| 4 | 1-methyl-imidazolyl | 29 | 80–83(1) | 53.6 | 53.4 | 5.1 | 5.1 | 23.4 | 23.3 | | |

The compounds prepared are identified as follows:

| Compound No. | Name |
|---|---|
| 1 | 1([4-methyl-5-(trifluoromethyl) 4H.1,2,4-triazol-3 yl]thio)-1-cyclopropanecarbonitrile |
| 2 | 1-[(4-phenyl-2-thiazolyl)thio]-1-cyclopropanecarbonitrile |
| 3 | 1-[(4-methyl-2-pyrimidinyl) thio]-1-cyclopropanecarbonitrile |
| 4 | 1-[(1-methyl-1H—imidazol-2-yl) thio]-1-cyclopropanecarbonitrile |

EXAMPLE 2

Seed plantings and the sequential application of the herbicide and safening agents are accomplished in the following manner:

A fumigated silt loam to top soil is placed in a container and compacted to a depth of approximately 1.27 cm. from the top of said container. A predetermined number of seeds of each of the crop species to be tested are placed on top of the soil. A quantity of soil sufficient to substantially fill the container is measured and placed in a second container. A measured quantity of the herbicide dispersed or dissolved in a suitable carrier is applied to the soil in the second container. A measured quantity of the safening agent dispersed or dissolved in a suitable carrier is thereafter sprayed on the soil already treated with the safening agent. The soil containing the safening agent and/or herbicide is thoroughly mixed. This mixing is sometimes referred to as incorporation of the herbicide and safening agent into the soil. The mixing or incorporation provides a substantially uniform distribution of the safening agent and herbicide throughout the soil. The seeds are covered with the soil containing the safening agent and/or herbicide or with untreated soil, and the pots are leveled. The pots are then placed on a sand bench in a greenhouse and watered from below as needed. When the seeds are treated with safener, the application of the safener to the soil is omitted. The coated seeds are placed on top of the soil in the pot and the balance of the treatment procedure is the same. The plants are observed at the end of approximately 21 days and the results in terms of percent inhibition of growth are recorded.

For each test series, a pot is also prepared containing no herbicide and no safening agent as a control. For each treatment, the herbicidal activity is observed on pots treated with the same quantity of herbicide alone. The results are observed and recorded as percent inhibition of each plant species tested. The tank mixes of know herbicides, safeners or combinations thereof were prepared by dissolving the appropriate amount of active ingredient in acetone. In Table 2 the results of testing the compounds of the present invention have been set forth. The rates of herbicide application are given in kilograms per hectare. In each treatment the amount of safener employed was 9.0 kilograms per hectare. In the % Plant Inhibition section of Table 2 under the listed crop columns the data are the inhibitions for herbicide plus safener on the left side and for the herbicide alone on the right side. The known herbicides are identified as follows. Throughout the examples, the herbicides are individually identified by reference numbers H-1 and H-2.

H-1 2-chloro-2',6'-diethyl-N-(methoxymethyl) acetanilide (alachlor)

H-2 2-chloro-2',6'-diethyl-N-(butoxymethyl) acetanilide (butachlor)

TABLE 2

| Herbicide No. | Rate | Compound No. | % Plant Inhibition Sorghum | Wheat | Rice |
|---|---|---|---|---|---|
| 1 | 2.2 | 1 | 100–90 | 75–90 | — |
| 1 | 2.2 | 2 | 45–80 | — | 95–90 |
| 1 | 2.2 | 3 | 95–85 | 90–75 | — |
| 1 | 2.2 | 4 | 20–85 | 100–80 | — |
| 2 | 4.5 | 1 | — | — | 95–90 |
| 2 | 4.5 | 2 | — | — | 90–75 |
| 2 | 4.5 | 3 | — | — | 40–60 |
| 2 | 4.5 | 4 | — | — | 95–90 |

The above examples illustrate that the 1-heterocyclicthio-1-cyclopropanecarbonitrile compounds of the present invention are useful in reducing herbicidal injury to certain crop plants. As indicated above, the safening agents may be applied to the plant locus as a mixture, i.e., a mixture of a herbicidally effective amount of herbicide and a safening effective amount of safening agent, or sequentially, i.e., the plant locus may be treated with an effective amount of the herbicide followed by a treatment with the safening agent or vice versa. The ratio of herbicide to safening agent may vary depending upon the crop to be protected, weeds to be inhibited, herbicide used, etc., but normally a herbicide to safening agent ratio ranging from 1:25 to 50:1 (preferably 1:5 to 15:1) parts by weight may be employed.

The amount of herbicide employed in the practice of the present invention will be at least an effective herbicidal amount. In general, effective herbicidal amounts are in the range of 0.2 and 12 kilograms/hectare. The preferred range of rate of application is from about 0.4 to about 10 kg/h. It will be appreciated that at times amounts either below or above these ranges will be necessary to obtain the best results. The selection of the herbicide to inhibit the emergence and growth of weeds depends upon the species of weeds to be controlled and the crop.

The herbicide, safening agent or mixture thereof may be applied to the plant locus alone or the herbicide, safening agent or mixture thereof may be applied in conjunction with a material referred to in the art as an adjuvant in liquid or solid form. Mixtures containing the appropriate herbicide and safening agent usually are prepared by admixing said herbicide and safening agent with an adjuvant including diluents, extenders, carriers and conditioning agents to provide compositions in the form of finely-divided particulate solids, granules, pellets, wettable powders, dusts, solutions and aqueous dispersions or emulsions. Thus, the mixture may include an adjuvant such as a finely-divided particulate solid, a solvent liquid of organic origin, water, a wetting agent, dispersing agent, or emulsifying agent or any suitable combination of these.

When applying the herbicide, safening agent or mixture thereof to the plant locus, useful finely-divided solid carriers and extenders include, for example, the talcs, clays, pumice, silica, diatomaceous earth, quartz, Fuller's earth, sulfur, powdered cork, powdered wood, walnut flour, chalk, tobacco dust, charcoal and the like. Typical liquid diluents useful include for example, Stoddard solvent, acetone, alcohols, glycols, ethyl acetate, benzene and the like. Such compositions, particularly liquids and wettable powders, usually contain as a conditioning agent one or more surface-active agents in amounts sufficient to render a given composition readily dispersible in water or in oil. By the term "surface-active agent", it is understood that wetting agents, dispersing agents, suspending agents and emulsifying agents are included therein. Such surface-active agents are well known and reference is made to U.S. Pat. No. 2,547,724, Columns 3 and 4, for detailed examples of the same.

Compositions of this invention generally contain from about 5 to 95 parts herbicide and safening agent, about 1 to 50 parts surface-active agent and about 4 to 94 parts solvent, all parts being by weight based on the total weight of the composition.

The application of the herbicide, safening agent or mixture thereof in a liquid or particulate solid form can be carried out by conventional techniques utilizing, for example, hand-carried or tractor-mounted spreaders, power dusters, boom and hand sprayers, spray dusters and granular applicators. The compositions can also be applied from aircraft as a dust or spray. If desired, application of the compositions of the invention to plants can be accomplished by incorporating the compositions in the soil or other media.

The crop may be protected by treating the crop seed with an effective amount of safening agent prior to planting. Generally, smaller amounts of safening agent are required to treat such seeds. A weight ratio of as little as 0.6 parts of safener per 1000 parts of seed may be effective. The amount of safener utilized in treating the seed may be increased if desired. Generally, however a weight ratio of safening agent to seed weight may range from 0.1 to 10.0 parts of safening agent per 1000 parts of seed. The determination of the effective amount of safening agent required is well within the skill of the art.

Since only a very samll amount of active safening agent is usually required for the seed treatment, the compound preferably is formulated as an organic solution, a powder, emulsifiable concentrate solution or flowable formulation, which can be diluted with water by the seed treater for use in seed treating apparatus. Of course, under certain conditions, it may be desirable to dissolve the safening agent in an organic solvent for use as a seed treatment or the pure compound alone may be used under properly controlled conditions.

There are thus also provided by this invention, novel seed treating compositions containing one or more of the described active safening agents intimately dispersed in an inert carrier or diluent for the intended use. Such carriers may be either solids, such as talc, clay, diatomaceous earth, sawdust, calcium carbonate, and the like or liquids such as water, kerosene, acetone, benzene, toluene, xylene, methylene chloride, and the like in which the active agent may be either dissolved or dispersed. Emulsifying agents are advisably used to achieve a suitable emulsion if two immiscible liquids are used as a carrier. Wetting agents may also be used to aid dispersing the active safening agent in liquids used as a carrier in which the agent is not completely soluble. Emulsifying agents and wetting agents are sold under numerous tradenames and trademarks and may be either pure compounds, mixtures of compounds of the same general groups, or they may be mixtures of compounds of different classes. Typical satisfactory surface active agents which may be used are alkali metal higher alkylarlyl sulfonates such as sodium dodecylbenzenesulfonate and the sodium salts of alkylnapthalene-sulfonic or sulfuric acid with n-aliphatic alcohols containing 8-18 carbon atoms, long chain quaternary ammonium compounds, sodium salts of petroleoum-derived alkylsulfonic acids, polyethylene sorbitan monooleate, alkylaryl polyether alcohols, water-soluble lignin sulfonate salts, alkali casein compositions, long chain alcohols usually containing 10-18 carbon atoms, and condensation products of ethylene oxide with fatty acids, alkylphenols and mercaptans.

The following examples illustrate the preparation of commercial seed treating compositions of the present invention.

EXAMPLE 3

The ingredients set forth in Table 3 are blended and then ground using a media mill to provide a particle size of less than 8-12 microns. The resulting flowable safening formulations can be used to treat the selected seeds by conventional means.

TABLE 3

| Ingredients | Compound 1 | Compound 2 | Compound 3 | Compound 4 |
|---|---|---|---|---|
| Safener | 40.0 | 35.0 | 40.0 | 42.0 |
| Koalinite | 1.5 | | 1.0 | |
| Silica aerogel | 3.0 | 4.0 | 3.5 | 3.5 |
| Sodium lignosulfate | | 3.5 | 3.0 | |
| Sodium N—methyl-N—oleyl taurate | | 2.0 | 2.5 | |
| Polyethylene glycol | 8.0 | | | 6.5 |
| Propylene glycol | 5.0 | 4.0 | 4.5 | |
| Water | 42.5 | 51.5 | 45.5 | 48.0 |

EXAMPLE 4

Twenty-five parts of Compound 3 and seventy-five parts of diethylene glycol monoethyl ether are blended; and the blended composition can be applied to seeds to be treated via mist application or by tumbling.

Although this invention has been described with respect to specific embodiments, the details thereof are not to be construed as limitations, for it is apparent that various equivalents, changes and modifications may be made without departing from the spirit and scope thereof; and it is understood that such equivalent embodiments are intended to be included herein.

What is claimed is:

1. A chemical compound having the structural formula:

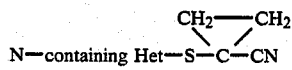

wherein N-containing Het is a radical selected from the group consisting of

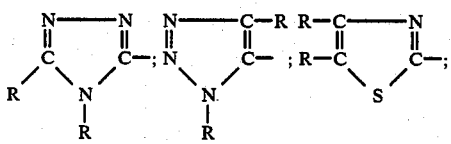

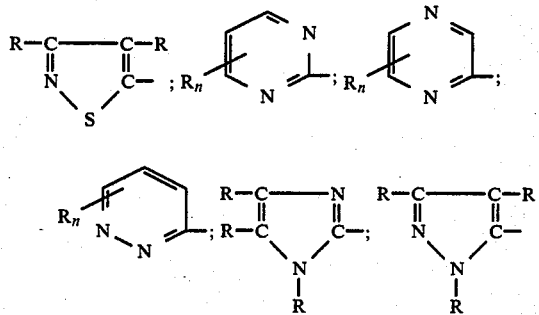

wherein R is individually selected from the group consisting of hydrogen, $C_1$-$C_5$ alkyl, $C_1$-$C_5$ alkoxy, $C_1$-$C_5$ haloalkyl, halogen, $C_1$-$C_5$ haloalkoxy, amino, phenyl, benzyl and phenyl substituted with up to three groups individually selected from the class consisting of $C_1$-$C_5$ alkyl, $C_1$-$C_5$ alkoxy, $C_1$-$C_5$ haloalkyl, nitro and halogen and n is 0-3.

2. The compound having the structural formula:

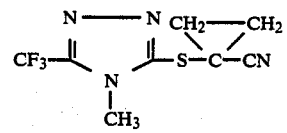

3. The compound having the structural formula:

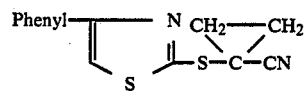

4. The compound having the structural formula:

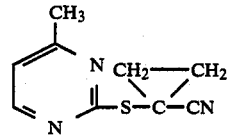

5. The compound having the structural formula:

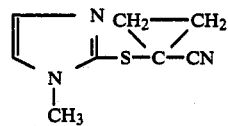

* * * * *